US00PP31608P2

(12) United States Plant Patent
Bradford et al.

(10) Patent No.: US PP31,608 P2
(45) Date of Patent: Mar. 31, 2020

(54) NECTARINE TREE NAMED 'SUMMER SUGARINE'

(50) Latin Name: *Prunus persica*
Varietal Denomination: Summer Sugarine

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 16/501,442

(22) Filed: Apr. 17, 2019

(51) Int. Cl.
*A01H 5/08* (2018.01)
*A01H 6/74* (2018.01)

(52) U.S. Cl.
USPC ..... Plt./190
CPC ..... *A01H 6/7454* (2018.05)

(58) Field of Classification Search
USPC ..... Plt./190
CPC ..... A01H 5/0856
See application file for complete search history.

(56) References Cited

U.S. PATENT DOCUMENTS

PP14,240 P2 10/2003 Bradford
PP16,494 P2 5/2006 Bradford
PP27,580 P2 1/2017 Bradford

*Primary Examiner* — Kent L Bell

(57) ABSTRACT

The present invention relates to a new and distinct variety of nectarine tree, *Prunus persica*, broadly characterized by a large size, vigorous, hardy, self-fertile, productive and regular bearing tree. The variety has a small non-showy blossom and blooms during the mid season, with a chilling requirement of about 550 hours. The fruit matures under the ecological conditions described in mid to late July, with first picking on Jul. 21, 2018. The fruit is uniform, very large in size, sub-acidic and sweet in flavor, globose to oblong in shape, clingstone in type, firm in texture, yellow in flesh color, red to orange in skin color, and has a bitter tasting kernel.

1 Drawing Sheet

Botanical classification: *Prunus persica.*
Variety denomination: 'SUMMER SUGARINE'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Summer Sugarine'.

The present variety was hybridized by us in 2005 as a first generation cross using 'Giant Pearl' (U.S. Plant Pat. No. 14,240) nectarine as the selected seed parent and 'Grand Bright' (U.S. Plant Pat. No. 16,494) nectarine as the selected pollen parent. Upon reaching maturity the fruit of this hybridization was gathered, and the seeds were removed, cracked, stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2010 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Giant Pearl' (U.S. Plant Pat. No. 14,240) nectarine by being vigorous, by being self-fertile, by having a small blossom, by having a bitter kernel, and by producing nectarines that are mostly red in skin color, that are clingstone in type, that are very large in size, and that are sub-acidic in flavor, but is quite distinguished from it by having globose instead of reniform leaf glands and by producing fruit that is yellow instead of white in flesh color and that ripens about twenty-six days earlier.

The present variety is similar to its pollen parent, 'Grand Bright' (U.S. Plant Pat. No. 16,494) nectarine, by being self-fertile and by producing nectarines that are mostly red in skin color, yellow in flesh color, and clingstone in type, but is quite distinguished from it by having a bitter instead of sweet kernel, by having globose instead of reniform leaf glands, and by producing fruit that is larger in size, that is sub-acidic instead of acidic in flavor, and that ripens about one week later.

The present variety is most similar to 'Candysweet XII' (U.S. Plant Pat. No. 27,580) nectarine by having a large size tree, by having globose leaf glands, by being self-fertile, by having a bitter kernel, by having a similar chilling requirement, and by producing nectarines that are mostly red in skin color, yellow in flesh color, clingstone in type, firm in texture, globose to slightly oblong in shape, and sweet in flavor, but is distinguished therefrom by having a small non-showy instead of large showy blossom and by producing nectarines that are larger in size and that mature about twenty-six days later.

SUMMARY OF VARIETY

In summary, the present nectarine variety is characterized by a large size, vigorous, hardy, self-fertile, productive and regular bearing tree. The variety has a small non-showy blossom and blooms during the mid season, with a chilling requirement of about 550 hours. The fruit matures under the ecological conditions described in mid to late July, with first picking on Jul. 21, 2018. The fruit is uniform, very large in size, sub-acidic and sweet in flavor, globose to oblong in shape, clingstone in type, firm in texture, yellow in flesh color, red to orange in skin color, and has a bitter tasting kernel.

DRAWING

The accompanying photograph consists of four whole fruits positioned to display the characteristics of the skin color and form, one divided fruit to reveal the flesh and stone, a tip shoot of new leaf growth, typical leaves, and two insets depicting the flower buds and blossoms as they appear on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 27, 2018, on the original tree during its thirteenth growing season. The blossom and flower descriptions were made the previous blooming season. All major color code designations are by reference to the Inter-Society Color Council, National Bureau of Standards. Common color names are also used occasionally.

PARENTAGE

Seed parent: 'Giant Pearl' (U.S. Plant Pat. No. 14,240) nectarine.

Pollen parent: 'Grand Bright' (U.S. Plant Pat. No. 16,494) nectarine.

TREE

Size: Large, reaching and maintaining a height of 12' [3.66 m.] and a spread of 12' [3.66 m.] after thirteen growing seasons utilizing typical dormant pruning.

Vigor: Vigorous, responding about average to irrigation and fertilization. The variety grows about 3' [0.91 m.] of surplus top-growth during the spring and summer. The plant should be grown on a standard commercial rootstock for production purposes.

Growth: Spreading and dense.

Form: Pruned to a vase shape.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-fertile.

Bearing: Regular bearer, with no crop failures observed.

Chilling requirement: About 550 hours.

Leaf bud burst: Medium, during the middle of flowering.

Trunk:

*Size*.—Medium, reaching a maximum diameter of 6½" [165.1 mm.] after the thirteenth growing season.

*Texture*.—Medium to shaggy.

*Bark color*.—A Grayish yellowish brown [80. gy.yBr] and Moderate yellowish brown [77. m.yBr] variegation with Dark grayish yellowish brown [81. d.gy.yBr] crevices present.

*Lenticels*.—Approximate Number Per Square Inch: 7. Color: Light grayish yellowish brown [79. l.gy.yBr]. Average Size: ¼" [6.4 mm.] in length. The width is typically one fourth as much as the length. Shape: Eye-shaped.

Branches:

*Size*.—Medium, diameter of main scaffold is 3½" [88.9 mm.] measured 12" above the crotch, diameter of limb is 1½" [38.1 mm.] measured 12" above the first fork.

*Texture*.—Smooth to medium on first and second year wood, increasing in roughness with age.

*Color*.—1st Year Wood Topside: Grayish red [19. gy.R]. 1st Year Wood Underside: Brilliant yellow green [116. brill.YG]. 2nd Year Wood: A Light grayish brown [60. l.gy.Br] and Grayish brown [61. gy.Br] variegation with Brownish orange [54. brO] crevices present.

*Lenticels*.—Number Per Square Inch: About 65 on second year wood. Color: Light yellowish brown [76. l.yBr]. Average Size: Medium, 1/16" [1.6 mm.] in length. The width is typically one fourth as much as the length. Shape: Eye-shaped.

Leaves:

*Size*.—Large to medium.

*Average length*.—6" [152.4 mm.].

*Average width*.—1½" [38.1 mm.].

*Arrangement*.—Alternate.

*Thickness*.—Medium.

*Form*.—Elliptical.

*Apex*.—Acuminate.

*Base*.—Acute with an average sixty-five degree angle.

*Surface*.—Smooth on both sides.

*Color*.—Dorsal Surface: Moderate olive green [125. m.OlG]. Ventral Surface: Moderate yellow green [120. m.YG].

*Red midvein*.—Absent.

*Margin*.—Finely serrate.

*Venation*.—Pinnately net veined.

*Petiole*.—Average Length: 7/16" [11.1 mm.]. Average Thickness: ⅛" [3.2 mm.]. Color: Strong yellow green [117. s.YG].

*Stipules*.—Number: 2 per leaf, up to 6 per growing tip. Average Length: ¼" [6.4 mm.]. Color: Vivid yellow green [115. v.YG] becoming Moderate brown [58. m.Br] with age.

*Glands*.—Number: 2 to 4 per leaf. Position: Alternate, first pair is located at the intersection of petiole and base of blade. Form: Globose. Size: Medium, about 1/32" [0.8 mm.] in length, about 1/64" [0.4 mm.] in width. Color: Strong yellow green [117. s.YG].

*Leaf buds*.—Pointed.

Flower buds:

*Hardiness*.—Hardy, with respect to central California blooming season.

*Diameter*.—Typically ⅜" [9.5 mm.] 1 week before bloom.

*Length*.—Typically ⅝" [15.9 mm.] 1 week before bloom.

*Form*.—Not appressed.

*Surface*.—Slightly pubescent.

*Tip color*.—Moderate purplish pink [250. m.pPk].

Flowers: Perfect, complete, perigynous, usually a single pistil, about thirty stamens, five sepal and petal locations alternately positioned.

*Type*.—Non-showy, small.

*Average flower diameter*.—15/16" [23.8 mm.].

*Average flower depth*.—5/16" [7.9 mm.] when fully open.

*Average pedicel length*.—⅛" [3.2 mm.].

*Number of petals*.—Mostly five, extra petal fragments common, double blossoms occasionally observed.

*Petal arrangement*.—Overlapping.

*Petal shape*.—Circular to ovate.

*Petal margin*.—Entire, somewhat wavy.

*Average petal diameter*.—⅜" [9.5 mm.].

*Average petal length*.—½" [12.7 mm.].

*Petal apex*.—Rounded to slightly obovate.

*Petal base*.—Rounded to somewhat truncate.

*Petal color*.—Moderate purplish pink [250. m.pPk] toward the apex, Dark purplish pink [251. d.pPk] toward the base on both sides.

*Anther color*.—Deep reddish orange [36. deep rO] at bloom onset.

*Pollen*.—Anthers produce an abundance of Brilliant yellow [83. brill.Y] pollen.

*Stigma color*.—Light greenish yellow [101. l.gY].

*Stigma position*.—Typically located about 1/16" [1.6 mm.] above nearby anthers.

*Stamen position*.—Typically located about ⅛" [3.2 mm.] above the petals.

*Ovary*.—Non-pubescent.

*Sepal color*.—Dark purplish red [259. d.pR] on the outer surface. The inner surface is a somewhat translucent Pinkish white [9. pkWhite] with both Grayish purplish red [262. gy.pR] and Vivid yellow green [115. v.YG] areas visible.

*Sepal length*.—7/32" [5.6 mm.].

*Sepal width*.—3/16" [4.8 mm.].

*Sepal apex*.—Rounded to elliptical to match the sepal length and width.

*Sepal margin*.—Fairly smooth.

*Average pistil length*.—11/16" [17.5 mm.].

*Average stamen length*.—7/16" [11.1 mm.].

*Fragrance*.—Moderate.

*Blooming period*.—Medium compared to other varieties, about two days before 'Grand Bright' (U.S. Plant Pat. No. 16,494) nectarine.

*Onset of bloom*.—One percent on Feb. 22, 2018.

*Date of full bloom*.—Mar. 4, 2018.

*Duration of bloom*.—One to two weeks, dependent on ambient temperature.

*Bloom density*.—Heavy.

*Number per cluster*.—1 to 3 with single flowers most common.

FRUIT

Maturity when described: Firm ripe, Jul. 27, 2018.

Date of first picking: Jul. 21, 2018.

Date of last picking: Jul. 30, 2018.

Size: Uniform, large.

*Average diameter axially*.—3½" [88.9 mm.].

*Average diameter across suture plane*.—3¼" [82.6 mm.].

*Average diameter across cheek plane*.—3¼" [82.6 mm.].

*Typical weight*.—11.7 ounces [332 grams].

Form: Uniform, globose to slightly oblong, mostly symmetrical.

*Longitudinal section form*.—Round to somewhat elongated.

*Axial view*.—Round.

Suture: A shallow groove extending from the base, along the side, and ending with a slight depression just beyond pistil point.

*Near the base*.—A shallow groove.

*Along the side*.—A shallow trough.

*Near the apex*.—A shallow groove.

Ventral surface: Rounded, lipped throughout on both sides.

Lips: Slightly unequal.

Cavity: Flaring with Strong orange yellow [68. s.OY] stem markings present.

*Depth*.—⅝" [15.9 mm.].

Breadth.—1⅛" [28.6 mm.].

Base: Truncate.

Apex: Rounded, somewhat cordate if viewed parallel to the suture.

Pistil point: An inconspicuous Pale orange yellow [73. p.OY] dot depressed within the suture of negligible length.

Stem: Medium.

*Average length*.—7/16" [11.1 mm.].

*Average width*.—3/16" [4.8 mm.].

Skin:

*Thickness*.—Medium.

*Surface*.—Smooth.

*Tenacity*.—Tenacious to the flesh.

*Astringency*.—Non-astringent.

*Tendency to crack*.—None observed.

*Color*.—Deep red [13. deep R] over a Strong reddish orange [35. s.rO] background with some Light yellow [86. l.Y] freckling toward the apex.

Flesh:

*Color*.—Brilliant orange yellow [67. brill.OY] with some Strong red [12. s.R] streaking toward the stone.

*Surface of pit cavity*.—Covered with Dark red [16. d.R] broken fibers when twisted away from the stone.

*Amygdalin*.—Scarce.

*Juice*.—Moderate.

*Texture*.—Firm.

*Fibers*.—Few, fine, tender.

*Ripens*.—Fairly even, slightly earlier on the shoulders.

*Flavor*.—Sub-acidic, sweet, typically 15 to 16 brix.
*Aroma*.—Moderate.
*Eating quality*.—Very good.

STONE

Type: Clingstone.
Form: Elliptical to oval.
Hilum: Narrow, oval.
Base: Rounded.
Apex: Acuminate.
Sides: Slightly Equal.
Tip: Acute, typically ⅛" [3.2 mm.] in length.
Surface: Irregularly furrowed toward the apex, pitted toward the base.
Ridges: Jagged.
External color: Moderate reddish brown [43. m.rBr] when first removed.
Pit wall color when cracked: Light brown [57. l.Br].
Cavity surface color: A Light brown [57. l.Br] and Strong brown [55. s.Br] two tone.
Average pit wall thickness: ¼" [6.4 mm.].
Average length: 1¾" [44.5 mm.].
Average width: 1¼" [31.8 mm.].
Average breadth: 1" [25.4 mm.].
Tendency to split: None observed.
Kernel:
*Form*.—Oval.
*Skin color*.—Pale yellow [89. p.Y].
*Pellicle color*.—Dark brown [59. d.Br].
*Vein color*.—Brilliant orange yellow [67. brill.OY].
*Taste*.—Bitter.
*Viable*.—Yes.
*Average length*.—⅞" [22.2 mm.].
*Average width*.—½" [12.7 mm.].
*Amygdalin*.—Abundant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to 'Candysweet XII' (U.S. Plant Pat. No. 27,580) nectarine by having a large size tree, by having globose leaf glands, by being self-fertile, by having a bitter kernel, by having a similar chilling requirement, and by producing nectarines that are mostly red in skin color, yellow in flesh color, clingstone in type, firm in texture, globose to slightly oblong in shape, and sweet in flavor, but is distinguished therefrom by having a small non-showy instead of large showy blossom and by producing nectarines that are larger in size and that mature about twenty-six days later.

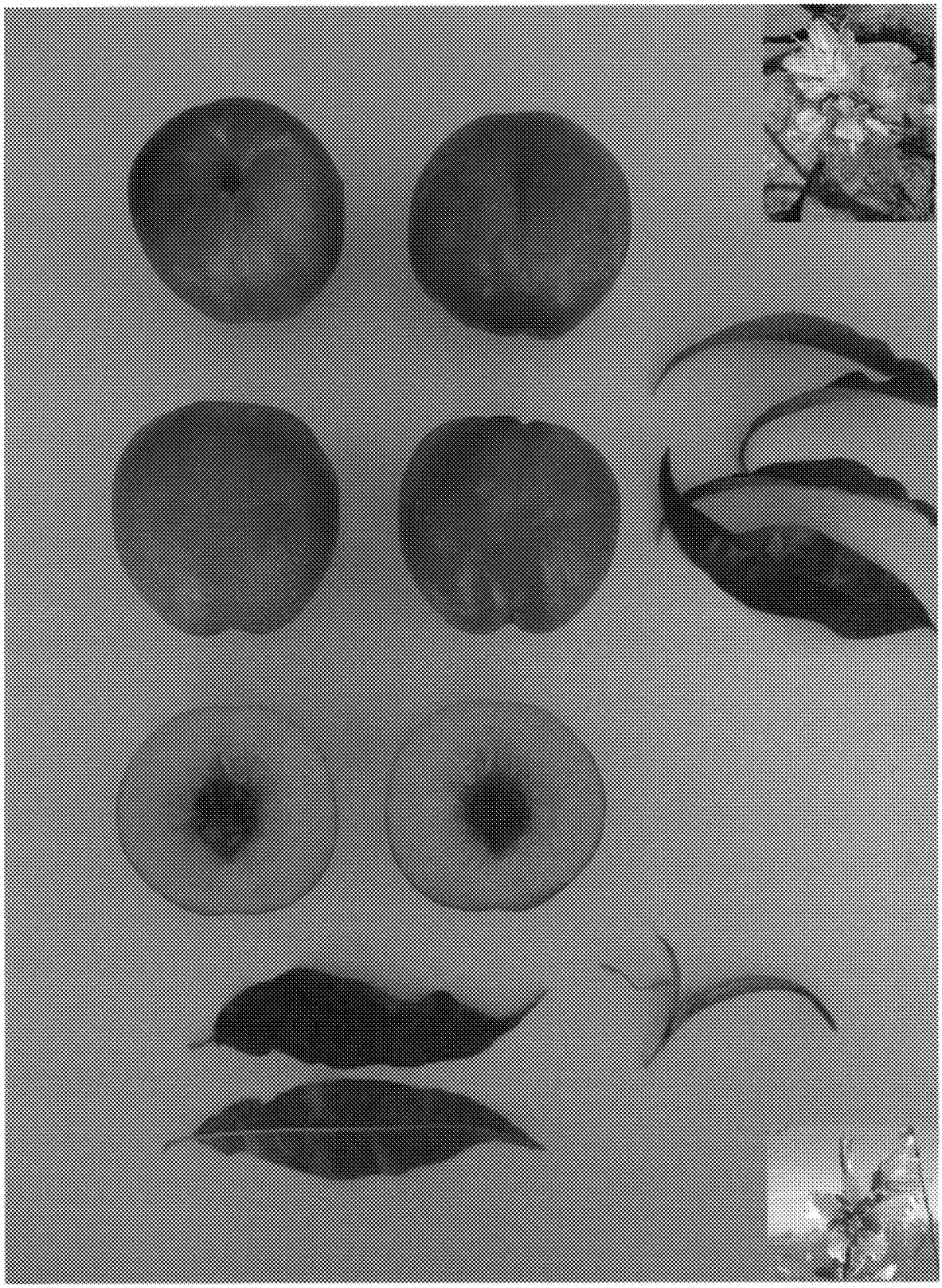

* * * * *